United States Patent [19]

Dumler et al.

[11] Patent Number: 5,436,164
[45] Date of Patent: Jul. 25, 1995

[54] ANALYTICAL METHOD FOR PARTICULATE SILICON

[75] Inventors: Richard C. Dumler, Breckenridge; Lydia L.-Y. Hwang, Midland; Maurice D. Lovay, Saginaw; Daniel P. Rice, Lothrop, all of Mich.

[73] Assignee: Hemlock Semi-Conductor Corporation, Hemlock, Mich.

[21] Appl. No.: 614,178

[22] Filed: Nov. 15, 1990

[51] Int. Cl.⁶ .................... G01N 21/35; G01N 21/64; C30B 13/14
[52] U.S. Cl. ........................ 436/72; 436/73; 436/103; 436/145; 436/171; 436/172; 436/174; 117/38; 117/49
[58] Field of Search ............... 436/72, 73, 103, 145, 436/171, 172, 174; 156/601, 607, 616.2, 620.4, 620.7, DIG. 64, DIG. 83; 117/14, 35, 38, 49, 933

[56] References Cited

U.S. PATENT DOCUMENTS

| 2,907,642 | 10/1959 | Rummel. | |
|---|---|---|---|
| 2,930,098 | 3/1960 | Emeis. | |
| 3,156,533 | 11/1964 | Imber. | |
| 4,200,621 | 4/1980 | Liaw et al. | 156/64 X |
| 4,572,668 | 2/1986 | Auth | 356/318 |
| 4,602,979 | 7/1986 | Marshall et al. | 156/DIG. 83 X |
| 4,809,196 | 2/1989 | Miller | 156/601 X |

Primary Examiner—Jeffrey R. Snay
Attorney, Agent, or Firm—William F. Boley

[57] ABSTRACT

The instant invention is a method for converting particulate silicon into monocrystalline silicon suitable for the determination of contaminates present in the particulate silicon. The method uses a silicon vessel, with known levels of the contaminates to be determined, to contain the particulate silicon. The silicon vessel, containing the particulate silicon, is float-zone processed to form a monolithic unit of monocrystalline silicon. The concentration of contaminates in the monocrystalline silicon can then be determined by the more sensitive analytical methods known for analysis of monolithic, monocrystalline silicon. The instant method is especially useful for measuring very low levels of aluminum, boron, phosphorous, and carbon in particulate silicon.

5 Claims, No Drawings

ANALYTICAL METHOD FOR PARTICULATE SILICON

BACKGROUND OF THE INVENTION

The present invention is a method for converting a sample of particulate silicon into monocrystalline silicon that is suitable for analysis of low-level contaminates present in the particulate silicon. The method uses a silicon vessel to retain the particulate silicon. The silicon vessel, containing the particulate silicon, is float-zone processed into monocrystalline silicon. The resultant monocrystalline silicon can then be analyzed by standard means for elemental impurities.

The production of semiconductor material for use in rectifiers, transistors, photo transistors, and the like requires extremely pure monocrystalline silicon. To control the quality of the monocrystalline silicon it is important to be able to assess the level of contaminates in the polycrystalline silicon from which the monocrystalline silicon is formed. Standard procedures for measuring the purity of high-purity silicon require a monocrystalline sample. This requirement presents problems when the polycrystalline silicon is in a particulate form.

The Czochralski method is a well known method for forming monocrystalline silicon in which particulate silicon is added to a heated quartz crucible to form a melt. A seed crystal is then contacted with the melt and slowly withdrawn to create a monocrystalline silicon rod. The problem with this technique of growing a monocrystalline silicon rod is that the silicon typically contains significant amounts of oxygen, carbon, boron, and other metallic impurities from the dissolution of some of the crucible wall during the crystal growth.

Rummel, U.S. Pat. No. 2,907,642, issued Oct. 6, 1959, describes a process whereby powdered silicon is blown into a melt zone to be incorporated therein and contribute to the formation of a monocrystalline silicon rod.

Emeis, U.S. Pat. No. 2,930,098, issued Mar. 29, 1960, proposed preparing particulate samples for possible float-zone treatment by sintering the particles in a quartz tube. The lower temperature required for sintering is reported to reduce contamination of the silicon due to deterioration of the quartz tube.

Imber, U.S. Pat. No. 3,156,533, issued Nov. 10, 1964, describes a process for converting powdered silicon into monocrystalline silicon with minimal contamination. The described invention relates to an apparatus for growing crystals which provides a conical crucible supported within a cylindrical chamber, and a powder dispensing means, or hopper suspended in the upper part of the chamber directly above the conically shaped crucible. A discharge opening in the apex of the conically-shaped crucible communicates with the lower part of the chamber where a seed crystal is supported directly beneath the opening. In operating the device, powder spills from the hopper onto the hot conical crucible where the powder melts and collects in a molten pool over the discharge opening of the cone. Drops form and fall through the opening to the crystal grown below.

None of the described procedures are entirely satisfactory for converting particulate silicon into monocrystalline silicon suitable for contaminates analysis. Processes which use a crucible to hold molten silicon result in contamination of the silicon, while non-crucible type processes are complicated and difficult to control. Therefore, it is an objective of the present invention to provide a method for float-zone processing of particulate silicon. It is a further objective to provide a method which reduces contamination during the conversion of polycrystalline silicon particles to monocrystalline, monolithic silicon. It is also an objective of the instant invention to provide a method, for determining contaminate levels of particulate silicon samples, which is reproducible and can be performed by means of standard equipment currently employed in float-zone processing.

SUMMARY OF THE INVENTION

The instant invention is a method for converting particulate silicon into monocrystalline silicon suitable for the determination of contaminates present in the particulate silicon. The method uses a silicon vessel to contain the particulate silicon. The silicon vessel, containing the particulate silicon, is float-zone processed to form a monolithic unit of monocrystalline silicon. The concentration of contaminates in the monocrystalline silicon can then be determined by the more sensitive analytical methods known for analysis of monolithic, monocrystalline silicon. The known contribution of the silicon vessel to the concentration of a contaminate is subtracted from the determined concentration value to arrive at a value for the concentration of a contaminate in the particulate silicon. The described method is especially useful for measuring low levels of aluminum, boron, phosphorous, carbon, and transition metals in particulate silicon.

DESCRIPTION OF THE INVENTION

The present invention is a method for preparing a monocrystalline silicon sample from particulate silicon, the prepared sample being particularly suitable for the analysis of low-level contaminates. What is claimed is a method for preparing monocrystalline silicon from particulate silicon, the method comprising:

(A) adding particulate silicon to a silicon vessel;
(B) float-zone processing the particulate silicon and silicon vessel into monocrystalline silicon; and
(C) determining the concentration of contaminates present in the monocrystalline silicon.

The source of the particulate silicon added to the silicon vessel is not critical. However, a significant advantage of the instant invention is that the sample is minimally contaminated by the method. Therefore, to realize the full advantage of the instant process, it is preferred that the particulate silicon be of an electronic grade or equivalent. The particulate silicon can be, for example, produced in a fluidized-bed process for chemical vapor deposition (CVD) of silane or chlorosilane to form polycrystalline silicon. The particulate silicon can be, for example, polycrystalline silicon particles resulting from the fragmentation of silicon forms produced in standard CVD processes. The particulate silicon can be monocrystalline particles or fragments.

The particulate silicon can be in the form of particles, pellets, chips, flakes, powders, or the equivalent. The size of the particulate silicon must be such that it will fit into the silicon vessel. Furthermore, the size or size range of the particulate silicon must be such that sufficient contact is established between the particles to allow adequate heat transfer to effect float-zone processing. For example, it is possible to float-zone process as large of pieces of silicon as will fit into the silicon vessel if the interstitial space between these pieces is filled with smaller particles of silicon. The lower limit of particle size is controlled only by the ability to handle the particulate silicon. A preferred size for the particulate silicon are those particles having a maximum dimension less than about one centimeter.

A silicon vessel is used to contain the particulate silicon and allow float-zone processing. The use of a silicon vessel in the float-zone process reduces contamination of the particulate silicon. Therefore, this process may be used to convert particulate silicon into monocrystalline silicon with low levels of contaminates. The monocrystalline silicon formed by this process is not necessarily limited to use as analytical samples, but may be employed for other uses known in the art which require high purity monocrystalline silicon.

By the term "silicon vessel" is meant any means, constructed essentially from silicon, which can contain silicon particles in a manner suitable for float-zone processing. The silicon vessel can be constructed from polycrystalline or monocrystalline silicon.

The size of the silicon vessel is dictated by the requirements of the apparatus used to perform the float-zone process. Any diameter for the silicon vessel, which is compatible with the float-zone apparatus employed, is acceptable. In general the thinner the walls of the silicon vessel the more desirable, since a reduction in vessel bulk minimizes the dilution of the sample during the float-zone process. In addition, it is preferred the vessel have a height sufficient to minimize the segregation of impurities caused by the float zone. It is preferred, that the silicon vessel have a height of at least about 7 cm. More preferred is a silicon vessel height of about 10 cm to 12 cm. The upper limit of the silicon vessel height is control by the limits imposed by the float-zone process and equipment.

The method of forming the silicon vessel is not considered critical to the instant invention. Any method which creates a vessel composed essentially of silicon and suitable for a float-zone process is acceptable. It is preferred that the method of forming the silicon vessel be chosen to minimize contamination of the silicon vessel. In a preferred embodiment, the silicon vessel is constructed by boring and removing a core from a polycrystalline silicon rod formed in a CVD process. The boring can be accomplished by, for example, a diamond tipped, stainless steel bore.

It is to be understood that, during float-zone processing, the silicon vessel and the particulate silicon blend in the melt zone to form a single growing crystal of silicon. Therefore, the final concentration of contaminates in the monocrystalline silicon ($C_t$) is a function of the weight of the silicon vessel ($M_v$), the concentration of the contaminates associated with the silicon from which the vessel is constructed ($C_v$), the weight of the particulate silicon sample ($M_s$), and the concentration of the contaminates associated with the particulate silicon sample ($C_s$). This relationship is expressed by the following equation:

$$C_t = \frac{(M_v)(C_v) + (M_s)(C_s)}{M_v + M_s} \quad (1)$$

Based on this relationship the concentration of a contaminate in a particulate silicon sample ($C_s$) is expressed by the equation:

$$C_s = \frac{C_t(M_v + M_s) - (M_v)(C_v)}{M_s} \quad (2)$$

Equations (1) and (2) demonstrate the importance of having a silicon vessel with a determinable and reproducible level of contaminates. Silicon readily picks up contaminates such as aluminum, boron, carbon, iron, and phosphorous during handling and processing. Therefore, concentrations of contaminates in the bulk material from which the silicon vessel is formed are typically not an accurate measurement of a contaminate's presence on or in the silicon vessel. Accordingly, it is preferred that the silicon vessels be cleaned to remove contaminates in a manner that allows reproducibility in the level of contaminates associated with vessels formed from the same bulk material. After obtaining vessels with reproducible low levels of contaminates, it is then preferred to establish the concentration of contaminates associated with the vessel ($C_v$) by float-zone processing several control vessels and determining contaminate levels in the resulting monocrystalline silicon.

The silicon vessels can be cleaned by standard methods for cleaning silicon, for example, solvent wash, acid etching, and water rinsing either alone or in any combination. It is important that the cleaning method be standardized to ensure reproducibility of residual contamination associated with control and sample containing silicon vessels. A preferred method for cleaning the silicon vessel is to etch with a mixture of hydrofluoric acid (HF) and nitric acid (HNO$_3$), followed by an etch with a mixture of HF, HNO$_3$, and acetic acid; with a distilled water rinse between each wash, and exhaustive rinsing after the last etch procedure.

The silicon vessel containing the particulate silicon is float-zone processed. The float-zone process can be any one of many processes described in the art and is not limited to those described herein. The float-zone process can be, for example, a process where the silicon vessel containing the particulate silicon is gripped at its open end and held vertically in a vacuum chamber or in a chamber filled with a protective gas. A small portion of the length of the silicon vessel containing particulate silicon is heated by a heating source, for example, an induction heating coil or a radiation heating source, so that a molten zone is formed at this point and, by relative movement between the heating source and the silicon vessel, the molten zone is passed through the silicon vessel and particulate silicon, from one end to the other.

If a seed crystal is contacted with the initial molten end of the silicon vessel, a silicon rod of monocrystalline silicon can be formed. The seed crystal may be a rod portion grown in monocrystalline form by previous treatment. The cross-sectional area of the monocrystalline silicon rod can be controlled or regulated by various measures. For example, the molten zone can be compressed or stretched by moving the end holding the crystal in relation to the end holding the silicon vessel toward or away from each other.

The monocrystalline silicon formed by this process is more suited for contaminates analysis by sensitive techniques, than the polycrystalline silicon particles. However, the monocrystalline silicon is equally suited for use in devices requiring monocrystalline silicon of high purity. If desired, additional passes of the heating source along the created monocrystalline silicon rod can be performed to effect purification of the silicon.

The most sensitive analytical method for determining concentration of contaminates in the monocrystalline silicon will depend upon the particular contaminate of interest. Typical contaminates of concern in monocrystalline silicon intended for semi-conductor type applications are, for example, aluminum, boron, phosphorous, iron, and carbon. The concentration of other contaminates, such as transition metals, may be determined as well. Measurements such as resistivity may be made directly on the formed rod of monocrystalline silicon. Precise measurement of aluminum, boron, and phosphorous concentrations can be made, for example, by means of photoluminescence analysis of etched wafers cut from the monocrystalline silicon rod. Standard procedures for photoluminescence analysis may be used, for example, those procedures described by Tajima, Jap. Ann. Rev. Electron. Comput. and Telecom. Semicond. Tech., p. 1–12, 1982. Carbon can be measured, for example, by Fourier Transformed infrared spectroscopy analysis of etched wafers cut from the monocrystalline silicon rod. Iron can be measured, for example, by atomic absorption spectroscopy of dissolved freeze-out tip solutions as described in Hwang et al., U.S. Pat. No. 4,912,528, issued Mar. 27, 1990.

The method of calculation of the concentration of a contaminate in the particulate sample is as previously described in equations (1) and (2).

The following examples are offered to facilitate a better understanding of the invention described herein. These examples are for illustrative purposes only and are not meant to limit the scope of the presently claimed invention.

EXAMPLE 1

The ability to prepare silicon vessels with reproducible levels of contaminates was demonstrated as follows. The silicon vessels were hollow cylinders, with one end closed, of about 10 cm height, with an internal diameter of 16.5 mm, and an external diameter of 19 mm. The silicon vessels were formed by coring a section of 19 mm polycrystalline silicon rod. The coring was performed by using a diamond tipped, stainless steel coring bit. After coring, the silicon vessels were extensively etched with a mixture of 49 percent hydrofluoric acid (HF) and 70 percent nitric acid ($HNO_3$), at a ratio of 1:8 volume/volume. The silicon vessels were further etched with a mixture of HF, $HNO_3$, and acetic acid at volume ratios of 1:3:1. Finally, the acid etched silicon vessels were exhaustively washed with distilled water. To determine the average background levels of aluminum, boron, phosphorous, and carbon of vessels prepared by this method, the etched vessels were fitted with plugs containing known concentrations of these contaminates. The vessels, with plugs, were float-zone processed in a 5 kW R.F. generator, Gas Siemens Zoner (Model VZA-3, Siemens Energy and Automation, Inc., East Brunswick, N.J.), at a coil speed of 2 mm/min., to produce monocrystalline silicon rods.

Wafers, of the monocrystalline silicon rod obtained by the float-zone process, were prepared for contaminates analysis. Prior to analysis, the wafers were etched in a mixture of nitric acid, hydrofluoric acid, and glacial acetic acid at volume ratios of 5.7:1.8:2.5, respectively, for about 10 minutes. The etched wafers were rinsed in distilled water and dried. The etched wafers were analyzed for the concentration of aluminum, boron, and phosphorous, by standard procedures using a photoluminescence spectrometer. Carbon contamination of the etched wafers was determined using Fourier Transformed infrared spectroscopy. The obtained values were corrected for contribution of the plugs to the aluminum, boron, phosphorous, and carbon concentration of the monocrystalline rods. Average values, in parts per billion (ppb), and standard deviations (S.D.) for the concentration of each contaminated associated with the silicon vessels were determined. Five silicon vessels were analyzed as described. The results are presented in Table 1.

TABLE 1

| Contaminates Concentrations of Silicon Vessels | | |
|---|---|---|
| Metal | ppb | S.D. |
| Aluminum | 0.097 | 0.078 |
| Boron | 0.035 | 0.008 |
| Phosphorous | 0.156 | 0.031 |
| Carbon | 90.0 | 60.0 |

The bulk material from which the silicon vessels were prepared typically had a concentration of boron of about 0.01 ppb, phosphorous about 0.03 ppb, aluminum less than about 0.015 ppb, and carbon less than about 50 ppb. Therefore, it is obvious that preparation of the silicon vessels has resulted in contamination of the silicon vessels. However, the small standard deviations demonstrate that the levels of contaminates, after careful vessel cleaning, are sufficiently uniform to establish a reproducible background value.

EXAMPLE 2.

Five replicate samples of polycrystalline silicon particles, prepared by CVD in a fluidized-bed process, were evaluated. The silicon particles had an average diameter less than about five millimeters. A sample of about 15 to 20 gm of the silicon particles was loaded into a silicon vessel, as described and prepared in Example 1. The silicon vessel, containing the particulate silicon, was placed in a float-zoning apparatus, as previously described. Float-zoning of the silicon vessel and particles was effected at a coil speed of about 2 mm/min. The resultant monocrystalline silicon rods had lengths of about 7 to 10 cm and diameters of 12 to 14 mm. Wafers of the monocrystalline silicon rods were cut from a position at least 3 cm from the seed-end of the rod. The wafers were etched in a mixture of nitric acid, hydrofluoric acid and glacial acetic acid at volume ratios of 5.7:1.8:2.5, respectively, for about 10 minutes. The etched wafers were rinsed in distilled water and analyzed for boron, phosphorous, and carbon as described in Example 1. The measured concentrations of boron, phosphorous, and carbon were corrected for the contribution from the vessel. The results are presented in Table 2.

TABLE 2

| Measurement of Particulate Silicon Contamination | | | |
|---|---|---|---|
| Sample | Boron (ppb) | Phosphorous (ppb) | Carbon (ppb) |
| 1 | 0.050 | <0.030 | 128 |
| 2 | 0.172 | 0.127 | 318 |
| 3 | 0.084 | 0.147 | 343 |
| 4 | 0.089 | 0.074 | 485 |
| 5 | 0.201 | 0.147 | 188 |

EXAMPLE 3.

Polycrystalline silicon chips and chunks were analyzed for boron, phosphorous, and carbon concentrations using the silicon vessel technique. A polycrystalline rod from a CVD process was fragmented and screened to a size range of 3 mm to 6 mm. About 15 to 20 gm of the sized silicon fragments was place in a silicon vessel as described and prepared in Example 1. Three replicate samples were analyzed. The silicon vessel, containing the sized silicon fragments, was float-zone processed, as previously described, and the concentration of boron, phosphorous, and carbon associated with the silicon fragments determined as previously described in Example 1. The results of these determinations are presented in Table 3.

TABLE 3

| Contaminates Content of Sized Silicon Fragments | | | |
|---|---|---|---|
| Sample | Boron (ppb) | Phosphorous (ppb) | Carbon (ppb) |
| 1 | 0.107 | 0.271 | <50 |
| 2 | 0.229 | 0.380 | 90 |
| 3 | 0.283 | 0.306 | 70 |

The data presented in Table 3 indicate that reproducible results can be obtain for boron, phosphorous, and carbon concentrations of silicon fragments, by the described process. The concentration of boron in the bulk material from which the silicon fragments were prepared was in the range of 0.01 to 0.03 ppb, the concentration of phosphorous was in the range of 0.1 to 0.2 ppb, and the concentration of carbon was less than about 50 ppb. This data also indicates that significant contamination of silicon can occur during the fragmentation and sizing of silicon, if appropriate controls are not used to control contamination.

What is claimed is:

1. A method of analyzing silicon particles for concentration of contaminates, the method comprising:
   (A) adding particulate silicon to a silicon vessel;
   (B) float-zone processing the particulate silicon and silicon vessel into monocrystalline silicon; and
   (C) determining concentration of contaminates present in the monocrystalline silicon.

2. The method of claim 1, where the contaminates are selected from the group consisting of aluminum, boron, phosphorous, and carbon.

3. The method of claim 1, where the contaminates are selected from the group consisting of aluminum, boron, and phosphorous and concentration of the contaminates in the monocrystalline silicon is determined by photoluminescence.

4. The method of claim 1, where the contaminate is carbon and concentration of the carbon in the monocrystalline silicon is determined by Fourier Transformed infrared spectroscopy.

5. A process for preparing monocrystalline silicon from particulate silicon comprising:
   (A) adding particulate silicon to a silicon vessel;
   (B) float-zone refining the particulate silicon and the silicon vessel to form monocrystalline silicon.

* * * * *